(12) United States Patent (10) Patent No.: US 7,988,883 B2
Wehner et al. (45) Date of Patent: Aug. 2, 2011

(54) HEAT TRANSFER COMPOSITIONS COMPRISING RENEWABLY-BASED BIODEGRADABLE 1,3-PROPANEDIOL

(75) Inventors: Ann Wehner, Hockessin, DE (US); Robert Miller, Wilmington, DE (US); Gyorgyi Fenyvesi, Wilmington, DE (US); Joseph W. DeSalvo, Lafayette Hill, PA (US); Melissa Joerger, Newark, DE (US)

(73) Assignee: DuPont Tate & Lyle Bio Products Company, LLC, Wilmington, DE (US)

( * ) Notice: Subject to any disclaimer, the term of this patent is extended or adjusted under 35 U.S.C. 154(b) by 926 days.

(21) Appl. No.: 11/705,212

(22) Filed: Feb. 12, 2007

(65) Prior Publication Data

US 2007/0200088 A1 Aug. 30, 2007

Related U.S. Application Data

(60) Provisional application No. 60/772,471, filed on Feb. 10, 2006, provisional application No. 60/772,194, filed on Feb. 10, 2006, provisional application No. 60/772,193, filed on Feb. 10, 2006, provisional application No. 60/772,111, filed on Feb. 10, 2006, provisional application No. 60/772,120, filed on Feb. 10, 2006, provisional application No. 60/772,110, filed on Feb. 10, 2006, provisional application No. 60/772,112, filed on Feb. 10, 2006, provisional application No. 60/846,948, filed on Sep. 25, 2006, provisional application No. 60/853,920, filed on Oct. 24, 2006, provisional application No. 60/859,264, filed on Nov. 15, 2006, provisional application No. 60/872,705, filed on Dec. 4, 2006, provisional application No. 60/880,824, filed on Jan. 17, 2007.

(51) Int. Cl.
*C09K 3/00* (2006.01)
*C09K 5/00* (2006.01)
*H01M 10/50* (2006.01)

(52) U.S. Cl. ............... 252/389.1; 252/73; 429/120
(58) Field of Classification Search ............ 252/73, 252/389.1; 429/120
See application file for complete search history.

(56) References Cited

U.S. PATENT DOCUMENTS

| | | | |
|---|---|---|---|
| 5,088,487 A | 2/1992 | Turner | |
| 5,194,159 A | 3/1993 | George et al. | |
| 5,633,362 A | 5/1997 | Nagarajan et al. | |
| 5,686,276 A | 11/1997 | Laffend et al. | |
| 5,772,912 A | 6/1998 | Lockyer et al. | |
| 5,821,092 A | 10/1998 | Nagarajan et al. | |
| 5,876,621 A | 3/1999 | Sapienza | |
| 5,968,407 A | 10/1999 | Boluk et al. | |
| 6,025,184 A | 2/2000 | Laffend et al. | |
| 6,136,576 A | 10/2000 | Diaz-Torres et al. | |
| 6,350,835 B1 | 2/2002 | O et al. | |
| 6,358,716 B1 | 3/2002 | Bulthuis et al. | |
| 6,361,983 B1 | 3/2002 | Ames | |
| 6,406,895 B1 | 6/2002 | Defretin et al. | |
| 6,428,767 B1 | 8/2002 | Burch et al. | |
| 6,479,716 B2 | 11/2002 | Hilaly et al. | |
| 6,538,164 B1 | 3/2003 | Gallagher et al. | |
| 6,555,700 B1 | 4/2003 | Horrobin et al. | |
| 6,596,189 B1 | 7/2003 | Moles et al. | |
| 6,635,188 B1 | 10/2003 | Berglund et al. | |
| 6,726,887 B1 | 4/2004 | Sugarman | |
| 6,742,345 B2 | 6/2004 | Carr | |
| 6,773,622 B1 | 8/2004 | Andrews et al. | |
| 6,818,146 B2 | 11/2004 | Eaton et al. | |
| 6,921,495 B2 | 7/2005 | Jeschke et al. | |
| 7,098,368 B2 | 8/2006 | Seapan et al. | |
| 7,169,321 B2 | 1/2007 | Simmons et al. | |
| 7,179,769 B2 | 2/2007 | Sunkara | |
| 7,214,329 B2 | 5/2007 | O | |
| 2002/0042131 A1 | 4/2002 | Brockbank et al. | |
| 2004/0105899 A1 | 6/2004 | Dowdle et al. | |
| 2005/0013753 A1 | 1/2005 | Eaton et al. | |
| 2005/0069997 A1 | 3/2005 | Adkesson et al. | |
| 2005/0109979 A1 | 5/2005 | Egawa et al. | |
| 2005/0130004 A1 | 6/2005 | Blunk et al. | |
| 2005/0154114 A1 | 7/2005 | Hale | |
| 2005/0244312 A1 | 11/2005 | Suppes et al. | |
| 2005/0245411 A1 | 11/2005 | Yang et al. | |
| 2006/0027782 A1 | 2/2006 | Wenderoth et al. | |
| 2006/0035808 A1 | 2/2006 | Ahmed et al. | |
| 2006/0076533 A1 | 4/2006 | Eaton et al. | |
| 2006/0110810 A1 | 5/2006 | Rajgarhia et al. | |
| 2006/0131544 A1 | 6/2006 | Scholer | |
| 2006/0148053 A1 | 7/2006 | Emptage et al. | |
| 2006/0180786 A1 | 8/2006 | Sapienza et al. | |
| 2006/0180793 A1 | 8/2006 | Wenderoth et al. | |

(Continued)

FOREIGN PATENT DOCUMENTS

EP 0562773 9/1993

(Continued)

OTHER PUBLICATIONS

Al-Hasani, S., et al. "Successful Embryo Transfer of Cryopreserved and In-Vitro Fertilized Rabbit Oocytes", Human Reproduction, vol. 4, No, 1, 1989, pp. 77-79.

(Continued)

*Primary Examiner* — Jafar Parsa (74) *Attorney, Agent, or Firm* — McCarter & English (57) ABSTRACT

Disclosed herein are heat transfer and antifreeze compositions comprising 1,3-propanediol, wherein the 1,3-propanediol in said heat transfer or antifreeze composition has a bio-based carbon content of about 1% to 100%. In addition, it is preferred that the 1,3-propanediol be biologically-derived, and wherein upon biodegradation, the biologically-derived 1,3-propanediol contributes no anthropogenic $CO_2$ emissions to the atmosphere.

28 Claims, 3 Drawing Sheets

U.S. PATENT DOCUMENTS

| | | |
|---|---|---|
| 2006/0192173 A1 | 8/2006 | Sunkara |
| 2006/0202156 A1 | 9/2006 | Sapienza et al. |
| 2007/0034825 A1 | 2/2007 | Wenderoth et al. |
| 2007/0075120 A1 | 4/2007 | Yang et al. |
| 2007/0075289 A1 | 4/2007 | Egawa et al. |

FOREIGN PATENT DOCUMENTS

| | | |
|---|---|---|
| EP | 0620971 | 10/1994 |
| EP | 1564225 | 8/2005 |
| JP | 2002138069 | 5/2002 |
| WO | WO9921736 | 5/1999 |
| WO | WO9960849 | 12/1999 |
| WO | WO0000568 | 1/2000 |
| WO | WO02073727 | 9/2002 |

OTHER PUBLICATIONS

Jabrane, S., et al. "Study of Thermal Behavior of 1,3-Propanediol and its Aqueous Solutions", Thermochimica Acta 311, (1998) pp. 121-127.

Fung, et al. "Evolution of Carbon Sinks in a Changing Climate"; PNAS, Aug. 9, 2005, vol. 12, No. 32; pp. 11201-11206.

Chen, et al. "Cyclization During Polyesterifications: Isolation of an 18-Member Ring Compound From Reaction of Phthalic Anhydride With 2,2-Dimethyl-1,3-Propanediol"; Journal of Applied Polymer Science, 1990, vol. 41, Issue 9-10, pp. 2517-2520.

"Industrial Bioproducts: Today and Tomorrow" (Paster et al.) Prepared by Energetics, Inc. for the US Department of Energy, Jul. 2003, See p. 1 and 2, Table 1-1 and 1-6.

| Product | Molecular weight | product | product | $CO_2$ fixated | $CO_2$ released | Anthropogenic emissions of $CO_2$ from Product Biodegradation |
|---|---|---|---|---|---|---|
| | g/mol | kg | mol | mol | mol | kg |
| EG | 62.068 | 1 | 16.1 | 0.0 | 32.2 | 1.4 |
| PG | 76.094 | 1 | 13.1 | 0.0 | 39.4 | 1.7 |
| Chem-PDO | 76.094 | 1 | 13.1 | 0.0 | 39.4 | 1.7 |
| Bio-PDO™ | 76.094 | 1 | 13.1 | 39.4 | 39.4 | 0.0 |

HEAT TRANSFER COMPOSITIONS COMPRISING RENEWABLY-BASED BIODEGRADABLE 1,3-PROPANEDIOL

CROSS REFERENCE TO RELATED APPLICATIONS

The present application claims the benefit of U.S. Provisional Application Ser. No. 60/772,471, filed Feb. 10, 2006; U.S. Provisional Application No. 60/772,194, filed Feb. 10, 2006, U.S. Provisional Application No. 60/772,193, filed Feb. 10, 2006, U.S. Provisional Application No. 60/772,111, filed Feb. 10, 2006, U.S. Provisional Application No. 60/772,120, filed Feb. 10, 2006, U.S. Provisional Application No. 60/772,110, filed Feb. 10, 2006, U.S. Provisional Application No. 60/772,112, filed Feb. 10, 2006, U.S. Provisional Application No. 60/846,948, filed Sep. 25, 2006, U.S. Provisional Application No. 60/853,920, filed Oct. 24, 2006, U.S. Provisional Application No. 60/859,264, filed Nov. 15, 2006, U.S. Provisional Application No. 60/872,705, filed Dec. 4, 2006 and U.S. Provisional Application No. 60/880,824, filed Jan. 17, 2007, the disclosures of which are expressly incorporated herein by reference in their entireties.

FIELD OF THE INVENTION

Disclosed herein are heat transfer and antifreeze compositions comprising 1,3-propanediol wherein the 1,3-propanediol in said heat transfer or antifreeze composition has a bio-based carbon content of about 1% to 100%. In addition, it is preferred that the 1,3-propanediol be biologically-derived, and wherein upon biodegradation, the biologically-derived 1,3-propanediol contributes no anthropogenic $CO_2$ emissions to the atmosphere.

BACKGROUND OF THE INVENTION

Consumers of heat transfer and, antifreeze consider many factors in selecting products for use. Recently certain factors have been a focus of and have driven scientific study and product development. These driving factors include, product safety, environmental impact, the extent to which the components are natural, and the aesthetic quality of the overall product. Therefore, manufacturers have to be concerned with the environmental impact of their products. In fact, the effort towards environmental impact awareness is a universal concern, recognized by government agencies. The Kyoto Protocol amendment to the United Nations Framework Convention on Climate Change (UNFCCC) currently signed by 156 nations is one example of a global effort to favor safer environmental manufacturing over cost and efficiency. When applied to heat transfer and antifreeze, consumers are increasingly selective about the origins of the products they purchase. The 2004 Co-operative Bank's annual Ethical Consumerism Report (www.co-operativebank.co.uk) disclosed a 30.3% increase in consumer spending on ethical retail products (a general classification for environmental safe, organic and fair trade goods) between 2003 and 2004 while total consumer spending during the same period rose only 3.7%.

Glycols such as ethylene glycol, propylene glycol, 1,3-butylene glycol, and 2-methyl-1,3-propanediol are biodegradable compounds useful in compositions ranging from cosmetics and personal care formulations to detergents to heat transfer compositions. While biodegradability is an important factor in protecting the environment, biodegradation of glycols derived from fossil-based sources has the unavoidable consequence of releasing previously fixed CO2 into the atmosphere. Thus, while glycols in general are advantageous for their biodegradability, the resulting global warming potential of fossil-based glycols during biodegradation is significant.

Carbon dioxide is singled out as the largest component of the collection of greenhouse gases in the atmosphere. The level of atmospheric carbon dioxide has increased 50% in the last two hundred years. Recent reports indicate that the current level of atmospheric carbon dioxide is higher than the peak level in the late Pleistocene, the epoch before modern humans (Siegenthaler, U. et al. Stable Carbon Cycle-Climate Relationship During the Late Pleistocene, Science, Vol. 310, no. 5752 (Nov. 25, 2005), pp. 1313-1317). Therefore, any further addition of carbon dioxide to the atmosphere is thought to further shift the effect of greenhouse gases from stabilization of global temperatures to that of heating. Consumers and environmental protection groups alike have identified industrial release of carbon into the atmosphere as the source of carbon causing the greenhouse effect.

Greenhouse gas emission can occur at any point during the lifetime of a product. Consumers and environmental groups consider the full lifespan of a product when evaluating a product's environmental impact. Consumers look for products that do not contribute new carbon to the atmosphere considering the environmental impact of production, use and degradation. Only organic products composed of carbon molecules from plant sugars and starches and ultimately atmospheric carbon are considered to not further contribute to the greenhouse effect.

In addition to adding carbon dioxide to the atmosphere, current methods of industrial production of glycols produce contaminants and waste products that include among them sulfuric acid, hydrochloric acid, hydrofluoric acid, phosphoric acid, oxalic acid tartaric acid, acetic acids, Alkali metals, alkaline earth metals, transitional metals and heavy metals, including Iron, cobalt, nickel, copper, silver, molybdenum, tungsten, vanadium, chromium, rhodium, palladium, osmium, iridium, rubidium, and platinum (U.S. Pat. Nos. 2,434,110, 5,034,134, 5,334,778, and 5,510,036).

Also of concern to consumers, especially consumers of heat transfer and antifreeze products, is an individual's reaction to such a product. The rate of development of hypersensitivity has markedly increased in the US in the last two decades. Many of these reactions are attributed to trace amount of substances. Other reactions are of idiopathic origin. Consumers seek products that are composed of ingredients of a more purified source and/or of all natural composition.

SUMMARY OF THE INVENTION

The present invention is directed to a heat transfer or antifreeze composition comprising 1,3-propanediol and a defoamer, wherein said 1,3-propanediol has a bio-based carbon content of at least 1%.

The present invention is further directed to a heat transfer or antifreeze composition comprising 1,3-propanediol and an anti-corrosive, wherein said 1,3-propanediol has a bio-based carbon content of at least 1%.

The present invention is also directed to a heat transfer or antifreeze composition comprising 1,3-propanediol wherein said 1,3-propanediol has an ultraviolet absorption at 220 nm of less than about 0.200 and at 250 nm of less than about 0.075 and at 275 nm of less than about 0.075.

The present invention is additionally directed to a heat transfer or antifreeze composition comprising 1,3-propanediol wherein said 1,3-propanediol has a concentration of total organic impurities of less than about 400 ppm.

The present invention is even further directed to a heat transfer or antifreeze composition comprising 1,3-propanediol, wherein the 1,3-propanediol in said composition has an anthropogenic $CO_2$ emission profile of zero upon biodegradation.

DETAILED DESCRIPTION OF THE INVENTION

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Compositions disclosed herein comprise 1,3-propanediol, having at least 1% bio-based carbon content, as greater as up to 100% of the glycol component of the composition. In one embodiment, the 1,3-propanediol comprises substantially all of the glycol component of the composition of the invention. In another embodiment, the 1,3-propanediol comprises all of the glycol component of the composition.

1,3-Propanediol

The terms "bioPDO", "biologically-derived, biodegradable 1,3-propanediol", "biologically derived 1,3-propanediol", "renewably-based 1,3-propanediol", "renewably-based, biodegradable 1,3-propanediol," "biosourced, and "biologically-produced 1,3-propanediol" and similar terms as used here in refer to 1,3-propanediol derived from microorganism metabolism of plant-derived sugars composed of carbon of atmospheric origin, and not composed of fossil-fuel carbon.

Anthropogenic $CO_2$ Emission Profile

Applicants' invention relates to heat transfer and antifreeze compositions comprising renewably-based, biodegradable 1,3-propanediol, in which said renewably-based, biodegradable 1,3-propanediol has an anthropogenic $CO_2$ emission profile of zero (0). An "anthropogenic emission profile" means anthropogenic $CO_2$ emissions that are contributed to the atmosphere upon biodegradation of a compound or composition. p "Biodegradable" or "Biodegradability" means the capacity of a compound to be broken down by living organisms to simple, stable compounds such as carbon dioxide and water.

Whereas photosynthesis is the process of creating growing matter through the conversion of carbon dioxide ($CO_2$) and water ($H_2O$) into plant material through the action of the sun, biodegradation is the process of converting organic material back into $CO_2$ and $H_2O$ through the activity of living organisms.

There are many published test methods for measuring the biodegradability of organic chemicals such as glycols. One internationally recognized method is ASTM E1720-01, Standard Test Method for Determining Ready, Ultimate Biodegradability of Organic Chemicals in a Sealed Vessel $CO_2$ Production Test.

Chemicals that demonstrate 60% biodegradation or better in this test method will biodegrade in most aerobic environments and are classified as ready biodegradable. All of the glycols referred to in this document meet this criteria.

Calculations setting forth the finding that the 1,3-propanediol of the present invention provides no anthropogenic COs emissions upon biodegradation is set forth below. A table in support of these calculations is provided in FIG. 3.

Figure 1:
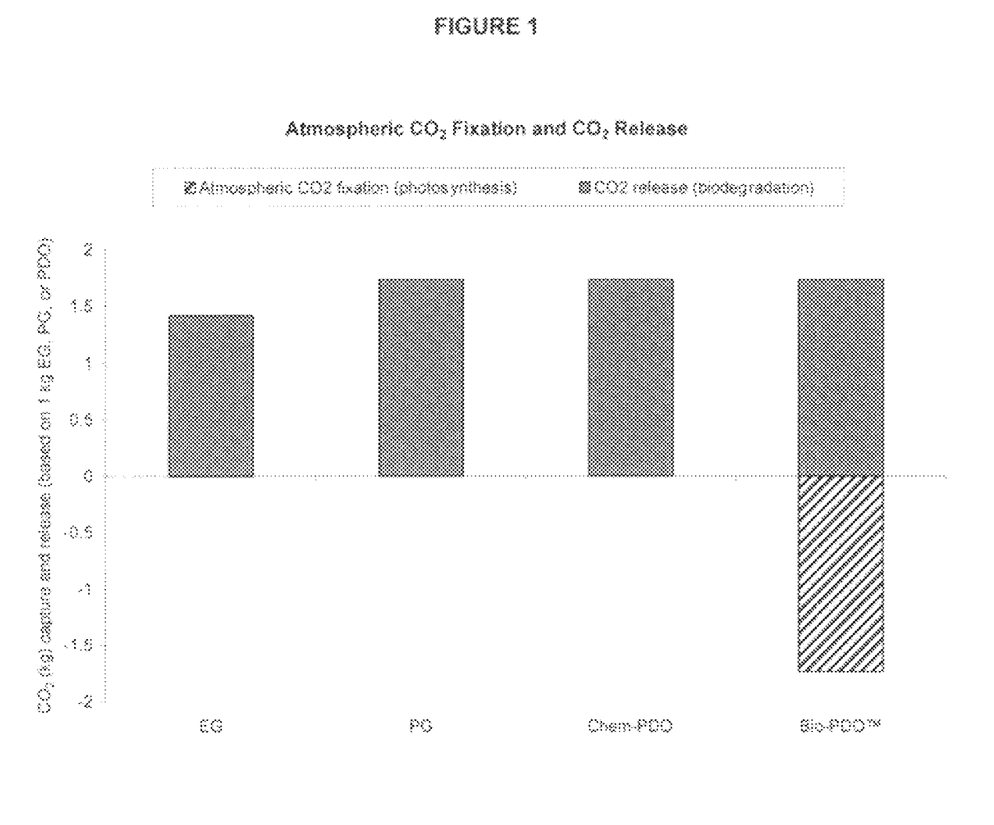
FIG. 1 is a graph showing $CO_2$ emissions for $CO_2$ fixation from the atmosphere during photosynthesis for renewably based 1,3-propanediol (Bio-PDO™) (−1.7 kg $CO_2$/kg product) and $CO_2$ release to the atmosphere during biodegradation (kg $CO_2$/kg product) for ethylene glycol (EG) (+1.4 kg $CO_2$/kg product), propylene glycol (PG) (+1.7 kg $CO_2$/kg product), fossil-based 1,3-propanediol (Chem-PDO) (+1.7 kg $CO_2$/kg product), and fermentatively-derived 1,3-propanediol (Bio-PDO™) (+1.7 kg $CO_2$/kg product).
Figure 2:
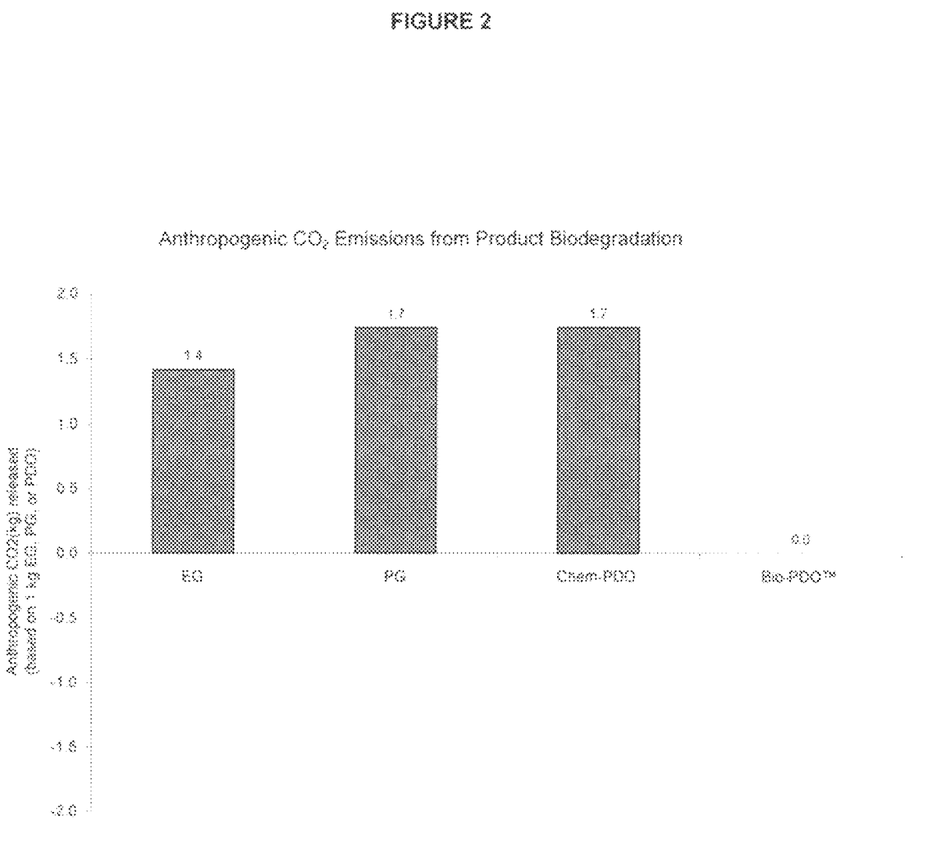
FIG. 2 is a graph showing that the net emissions of $CO_2$ to the atmosphere for renewably based 1,3-propanediol (Bio-PDO) is zero (0).
Figure 3:
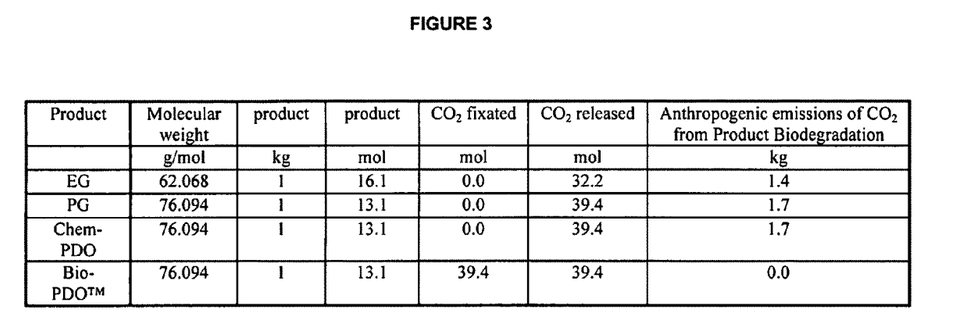
FIG. 3 is a table that shows the calculations for the data shown in FIGS. 1 and 2.

When one molecule of 1,3-propanediol degrades, three molecules of $CO_2$ are released into the atmosphere. Because all of these molecules of $CO_2$ released during degradation from "fermentatively-derived" 1,3-propanediol have an atmospheric origin, the net release of $CO_2$ to the atmosphere is thus zero. Comparatively, because a fossil fuel-derived propylene glycol and fossil-derived 1,3-propanediol contains three carbon atoms which originate from a fixed carbon source (i.e., the fossil fuel), degradation of one molecule of fossil fuel-derived propylene glycol or 1,3-propanediol results in a net release of three molecules of $CO_2$ into the atmosphere. Similarly, because fossil fuel-derived ethylene glycol contains two carbon atoms, which originate from a fixed carbon source, degradation of one molecule of fossil fuel-derived ethylene glycol results in a net release of two molecules of $CO_2$ into the atmosphere.

In order to quantify the $CO_2$ released for one kilogram of each ethylene glycol, propylene glycol, chemical 1,3-propanediol and "fermentatively-derived" 1,3 propanediol (Bio-PDO™), the product weight (1 kg) is divided by its molecular weight. For each carbon atom present in the molecule, one molecule of $CO_2$ is released. The molecules of $CO_2$ are multiplied by the molecular weight of $CO_2$ (44 kg/kmole) to quantify the impact of $CO_2$ release (kg) per one unit (kg) of product.

Fossil-Fuel Based Carbon Feedstock Release 1 kg of fossil fuel derived ethylene glycol*(1 kmol EG/62.068 kg)*(2 kmol $CO_2$/1 kmol EG)*(44 kg $CO_2$/kmol $CO_2$)=1.4 kg $CO_2$ 1 kg of fossil fuel derived propylene glycol*(1 kmol PG/76.094 kg)*(3 kmol $CO_2$/1 kmol PG)*(44 kg $CO_2$/kmol $CO_2$)=1.7 kg $CO_2$ 1 kg of fossil fuel derived 1,3-propanediol*(1 kmol chem-PDO/76.094 kg)*(3 kmol $CO_2$/1 kmol chem-PDO)*(44 kg $CO_2$/kmol $CO_2$)=1.7 kg $CO_2$ Bio-Based Carbon Feedstock Balance Capture:

1 kg of Bio-PDO™*(1 kmol Bio-PDO™/76.094 kg)*(−3 kmol $CO_2$/1 kmol Bio-PDO™)*(44 kg $CO_2$/kmol $CO_2$)=−1.7 kg $CO_2$ Release:

1 kg of Bio-PDO™*(1 kmol Bio-PDO™/76.094 kg)*(3 kmol $CO_2$/1 kmol Bio-PDO™)*(44 kg $CO_2$/kmol $CO_2$)=1.7 kg $CO_2$ Net:

−1.7 kg+1.7 kg=0 kg

This Bio-based Carbon Feedstock Balance result demonstrates that there are no anthropogenic CO2 emissions from the biodegradation of the renewably sourced Bio-PDO. The term "anthropogenic" means man-made or fossil-derived.

Bio-Based Carbon

"Carbon of atmospheric origin" as used herein refers to carbon atoms from carbon dioxide molecules that have recently, in the last few decades, been free in the earth's atmosphere. Such carbons in mass are identifiable by the present of particular radioisotopes as described herein. "Green carbon", "atmospheric carbon", "environmentally friendly carbon", "life-cycle carbon", "non-fossil fuel based carbon", "non-petroleum based carbon", "carbon of atmospheric origin", and "biobased carbon" are used synonymously herein.

"Carbon of fossil origin" as used herein refers to carbon of petrochemical origin. Such carbon has not been exposed to UV rays as atmospheric carbon has, therefore masses of carbon of fossil origin has few radioisotopes in their population. Carbon of fossil origin is identifiable by means described herein. "Fossil fuel carbon", "fossil carbon", "polluting carbon", "petrochemical carbon", "petro-carbon" and carbon of fossil origin are used synonymously herein.

The abbreviation "IRMS" refers to measurements of CO2 by high precision stable isotope ratio mass spectrometry.

The term "carbon substrate" means any carbon source capable of being metabolized by a microorganism wherein the substrate contains at least one carbon atom.

"Renewably-based" denotes that the carbon content of the 1,3-propanediol is from a "new carbon" source as measured by ASTM test method D 6866-05 Determining the Biobased Content of Natural Range Materials Using Radiocarbon and Isotope Ratio Mass Spectrometry Analysis, incorporated herein by reference. This test method measures the C-14/C-12 isotope ratio in a sample and compares it to the C-14/C-12 isotope ratio in a standard 100% biobased material to give percent biobased content of the sample. "Biobased materials" are organic materials in which the carbon comes from recently (on a human time scale) fixated $CO_2$ present in the atmosphere using sunlight energy (photosynthesis). On land, this $CO_2$ is captured or fixated by plant life (e.g., agricultural crops or forestry materials). In the oceans, the $CO_2$ is captured or fixated by photosynthesizing bacteria or phytoplankton. A biobased material has a C-14/C-12 isotope ratio in range of from 1:0 to greater than 0:1. Contrarily, a fossil-based material, has a C-14/C-12 isotope ratio of 0:1.

A small amount of the carbon dioxide in the atmosphere is radioactive. This 14C carbon dioxide is created when nitrogen is struck by an ultra-violet light produced neutron, causing the nitrogen to lose a proton and form carbon of molecular weight 14 which is immediately oxidized in carbon dioxide. This radioactive isotope represents a small but measurable fraction of atmospheric carbon. Atmospheric carbon dioxide is cycled by green plants to make organic molecules during the process known as photosynthesis. The cycle is completed when the green plants or other forms of life metabolize the organic molecules producing carbon dioxide which is released back to the atmosphere. Virtually all forms of life on Earth depend on this green plant production of organic molecule to produce the chemical energy that facilitates growth and reproduction. Therefore, the 14C that exists in the atmosphere becomes part of all life forms, and their biological products. These renewably based organic molecules that biodegrade to CO2 do not contribute to global warming as there is no net increase of carbon emitted to the atmosphere. In contrast, fossil fuel based carbon does not have the signature radiocarbon ratio of atmospheric carbon dioxide.

Atmospheric origin and fixed carbon source as used herein are relative terms in that the time period of when CO2 is of atmospheric or fixed origin relates to the life cycle of the 1,3-propanediol. Thus, while it is quite possible that, at one time, carbon from a fossil fuel was found in the atmosphere (and, as a corollary, that atmospheric CO2 may one day be incorporated into a fixed carbon source), for purposes herein carbon is considered to be from a fixed carbon source until it is released into the atmosphere by degradation.

Assessment of the renewably based carbon in a material can be performed through standard test methods. Using radiocarbon and isotope ratio mass spectrometry analysis, the biobased content of materials can be determined. ASTM International, formally known as the American Society for Testing and Materials, has established a standard method for assessing the biobased content of materials. The ASTM method is designated ASTM-D6866.

The application of ASTM-D6866 to derive a "biobased content" is built on the same concepts as radiocarbon dating, but without use of the age equations. The analysis is performed by deriving a ratio of the amount of radiocarbon (14C) in an unknown sample to that of a modem reference standard. The ratio is reported as a percentage with the units "pMC" (percent modern carbon). If the material being analyzed is a mixture of present day radiocarbon and fossil carbon (containing no radiocarbon), then the pMC value obtained correlates directly to the amount of Biomass material present in the sample.

The modern reference standard used in radiocarbon dating is a NIST (National Institute of Standards and Technology) standard with a known radiocarbon content equivalent approximately to the year AD 1950. AD 1950 was chosen since it represented a time prior to thermo-nuclear weapons testing which introduced large amounts of excess radiocarbon into the atmosphere with each explosion (termed "bomb carbon"). The AD 1950 reference represents 100 pMC.

"Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. It's gradually decreased over time with today's value being near 107.5 pMC. This means that a fresh biomass material such as corn could give a radiocarbon signature near 107.5 pMC.

Combining fossil carbon with present day carbon into a material will result in a dilution of the present day pMC content. By presuming 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, it would give a radiocarbon signature near 54 pMC.

A biomass content result is derived by assigning 100% equal to 107.5 pMC and 0% equal to 0 pMC. In this regard, a sample measuring 99 pMC will give an equivalent biobased content result of 93%.

A sample of "fermentatively-derived" 1,3-propanediol was submitted by DuPont to Iowa State University for biobased content analysis using ASTM method D 6866-05. The results received from Iowa State University demonstrated that the above sample was 100% bio-based content (ref: Norton, Glenn. Results of Radiocarbon Analyses on samples from DuPont Bio-Based Materials—reported 07-08-05).

Assessment of the materials described herein were done in accordance with ASTM-D6866. The mean values quoted in this report encompasses an absolute range of 6% (plus and minus 3% on either side of the biobased content value) to account for variations in end-component radiocarbon signatures. It is presumed that all materials are present day or fossil in origin and that the desired result is the amount of biobased component "present" in the material, not the amount of biobased material "used" in the manufacturing process.

Results of Radiocarbon Analyses on Samples from DuPont Bio-Based

| Materials Reported Jul. 8, 2005 | |
| --- | --- |
| PRODUCT | BIOBASED CONTENT (%) |
| 1,3-Propanediol | 100 |

There may be certain instances wherein a heat transfer and antifreeze composition of the invention may comprise a combination of a biologically-derived 1,3-propanediol and one or more non biologically-derived glycol components, such as, for example, chemically synthesized 1,3-propanediol. In such occasions, it may be difficult, if not impossible to determine which percentage of the glycol composition is biologically-derived, other than by calculating the bio-based carbon content of the glycol component. In this regard, in the heat transfer and antifreeze compositions of the invention, the glycol component, and in particular, the 1,3-propanediol, can comprise at least about 1% bio-based carbon content up to 100% bio-based carbon content, and any percentage therebetween.

Purity

"Substantially purified," as used by applicants to describe the biologically-produced 1,3-propanediol produced by the process of the invention, denotes a composition comprising 1,3-propanediol having at least one of the following characteristics: 1) an ultraviolet absorption at 220 nm of less than about 0.200 and at 250 nm of less than about 0.075 and at 275 nm of less than about 0.075; or 2) a composition having L*a*b* "b*" color value of less than about 0.15 and an absorbance at 270 nm of less than about 0.075; or 3) a peroxide composition of less than about 10 ppm; or 4) a concentration of total organic impurities of less than about 400 ppm.

A "b*" value is the spectrophotometrically determined "Yellow Blue measurement as defined by the CIE L*a*b* measurement ASTM D6290.

The abbreviation "AMS" refers to accelerator mass spectrometry.

By the acronym "NMR" is meant nuclear magnetic resonance.

By the terms "color" and "color bodies" is meant the existence of visible color that can be quantified using a spectrocolorimeter in the range of visible light, using wavelengths of approximately 400-800 nm, and by comparison with pure water. Reaction conditions can have an important effect on the nature of color production. Examples of relevant conditions include the temperatures used, the catalyst and amount of catalyst. While not wishing to be bound by theory, we believe color precursors include trace amounts of impurities comprising olefinic bonds, acetals and other carbonyl compounds, peroxides, etc. At least some of these impurities may be detected by such methods as UV spectroscopy, or peroxide titration.

"Color index" refers to an analytic measure of the electromagnetic radiation-absorbing properties of a substance or compound.

Biologically-derived 1,3-propanediol useful in heat transfer and antifreeze compositions disclosed herein has at least one of the following characteristics: 1) an ultraviolet absorption at 220 nm of less than about 0.200 and at 250 nm of less than about 0.075 and at 275 nm of less than about 0.075; or 2) a composition having L*a*b* "b*" color value of less than about 0.15 and an absorbance at 270 nm of less than about 0.075; or 3) a peroxide composition of less than about 10 ppm; or 4) a concentration of total organic impurities of less than about 400 ppm. A "b*" value is the spectrophotometrically determined Yellow Blue measurement as defined by the CIE L*a*b* measurement ASTM D6290.

The level of 1,3-propanediol purity can be characterized in a number of different ways. For example, measuring the remaining levels of contaminating organic impurities is one useful measure. Biologically-derived 1,3-propanediol can have a purity level of less than about 400 ppm total organic contaminants; preferably less than about 300 ppm; and most preferably less than about 150 ppm. The term ppm total organic purity refers to parts per million levels of carbon-containing compounds (other than 1,3-propanediol) as measured by gas chromatography.

Biologically-derived 1,3-propanediol can also be characterized using a number of other parameters, such as ultraviolet light absorbance at varying wavelengths. The wavelengths 220 nm, 240 nm and 270 nm have been found to be useful in determining purity levels of the composition. Biologically-derived 1,3-propanediol can have a purity level wherein the UV absorption at 220 nm is less than about 0.200 and at 240 nm is less than about 0.075 and at 270 nm is less than about 0.075.

Biologically-derived 1,3-propanediol can have a b* color value (CIE L*a*b*) of less than about 0.15.

The purity of biologically-derived 1,3-propanediol compositions can also be assessed in a meaningful way by measuring levels of peroxide. Biologically-derived 1,3-propanediol can have a concentration of peroxide of less than about 10 ppm.

It is believed that the aforementioned purity level parameters for biologically-derived and purified 1,3-propanediol (using methods similar or comparable to those disclosed in U.S. Patent Application No. 2005/0069997) distinguishes such compositions from 1,3-propanediol compositions prepared from chemically purified 1,3-propanediol derived from petroleum sources, as per the prior art.

Fermentation

"Biologically produced" means organic compounds produced by one or more species or strains of living organisms, including particularly strains of bacteria, yeast, fungus and other microbes. "Bio-produced" and biologically produced are used synonymously herein. Such organic compounds are composed of carbon from atmospheric carbon dioxide converted to sugars and starches by green plants.

"Biologically-based" means that the organic compound is synthesized from biologically produced organic components. It is further contemplated that the synthesis process disclosed herein is capable of effectively synthesizing other monoesters and diesters from bio-produced alcohols other than 1,3-propanediol; particularly including ethylene glycol, diethylene glycol, triethylene glycol, 1,2-propylene glycol, dipropylene diol, tripropylene diol, 2-methyl 1,3-propanediol, neopentyl glycol and bisphenol A. "Bio-based", and "bio-sourced"; "biologically derived"; and "bio-derived" are used synonymously herein.

"Fermentation" as used refers to the process of metabolizing simple sugars into other organic compounds. As used herein fermentation specifically refers to the metabolism of plant derived sugars, such sugar are composed of carbon of atmospheric origin.

Biologically-derived 1,3-propanediol can be obtained based upon use of the fermentation broth ("fermentatively-derived") generated by a genetically-engineered *Eschericia coli* (*E. coli*) previously disclosed in, for example, U.S. Pat. No. 5,686,276. However, other single organisms, or combinations of organisms, may be used to biologically produce 1,3-propanediol, using organisms that have been genetically-engineered according to methods known in the art. "Fermentation" refers to a system that catalyzes a reaction between substrate(s) and other nutrients to product(s) through use of a biocatalyst. The biocatalysts can be a whole organism, an isolated enzyme, or any combination or component thereof that is enzymatically active. Fermentation systems useful for producing and purifying biologically-derived 1,3-propanediol are disclosed in, for example, Published U.S. Patent Application No. 2005/0069997 incorporated herein by reference.

The biologically derived 1,3-propanediol (Bio-PDO) for use in the current invention, produced by the process described herein, contains carbon from the atmosphere incorporated by plants, which compose the feedstock for the production of Bio-PDO. In this way, the Bio-PDO used in the compositions of the invention contains only renewable carbon, and not fossil fuel based, or petroleum based carbon. Therefore the compositions of the invention have less impact on the environment as the propanediol used in the compositions does not deplete diminishing fossil fuels and, upon degradation releases carbon back to the atmosphere for use by plants once again. Thus, the present invention can be characterized as more natural and having less environmental impact than similar compositions comprising petroleum based glycols.

Moreover, as the purity of the Bio-PDO utilized in the compositions of the invention is higher than chemically synthesized 1,3-propanediol and other glycols, risk of introducing impurities that may cause irritation is reduced by its use over commonly used glycols, such as propylene glycol.

This 1,3-propanediol of the invention can be isolated from the fermentation broth and is incorporated into heat transfer and antifreeze compositions of the invention, by processes as are known to those of ordinary skill in the applicable art.
Renewably-Based, Biodegradable 1,3-propanediol-Containing Compositions As mentioned above, Bio-PDO can be incorporated into numerous compositions as a glycol component. For example, Bio-PDO can be part of or the sole glycol component of deicing compositions and anti-icing compositions.

It is contemplated herein that other renewably-based or biologically-derived glycols, such as ethylene glycol, dietheylene glycol, triethylene glycol, 1,2 propylene glycol, dipropylene glycol, tripopylene glycol, neopentyle glycol and bisphenol A, among others, can be used in the heat transfer and coolant compositions of the present invention.

The term "heat transfer fluid" as used herein refers to a fluid or liquid that is capable of transferring and/or dissipating a quantity of thermal energy from a first point to second point. Heat transfer fluids include coolants.

Heat transfer fluid as used herein may include both concentrated solutions of Bio-PDO mixtures as well as to diluted solutions of the same mixed with water, preferably deionized water. It will be appreciated that although heat transfer fluid may be purchased, transported or used in concentrated solutions, such concentrates will often be diluted with water, especially deionized water, prior to incorporation or use in, for example, a fuel cell. Exemplary heat transfer composition include, but are not limited to, heating medium for radiant heating systems and industrial heating applications, and Heating, Ventilation, and Air Conditioning applications, and thermal energy storage, heating and cooling. Heat transfer fluids can also be used in a variety of markets, including vehicles and equipment (as antifreeze), process manufacturing industries (e.g., chemicals, pharmaceuticals, plastics, fiber and food), energy production, asphalt, laundry, biotechnology, cryogenic preservation, metalworking, mining, ice rinks, refrigeration systems and heating systems, metalworking, transportation, mining and others such as ice rinks.

In heat transfer compositions, the glycol is typically the major component of the composition, present in a range of from about 1% to about 100%.

In antifreeze compositions, the glycol is typically the major component of the composition, present in a range of from about 1% to about 100%.

In the heat transfer and antifreeze compositions of the invention, the Bio-PDO can be the major component of the composition, present in amounts up to 100% by weight based on the weight of the total composition. The amount of Bio-PDO used in the products is generally the balance after adding the percentages of typical ingredients such as corrosion inhibitors, foam suppressants, dyes and water, Those of ordinary skill in the art will now understand that, under appropriate circumstances, considering issues such as corrosion, toxicity, viscosity, fluid life, equipment specifications, fluid color, cost, etc., other elements, such as for example, one or more of a colorant, a wetting agent, an antifoam agent, a biocide, a bitterant, a nonionic dispersant, anti-foam agents, anti-icing additives, anti-wear additives, demulsifiers, detergents, dispersants, emulsifiers, EP additives, oiliness agents, oxidation inhibitors, pour point depressants, rust inhibitors, tackiness agents, viscosity improvers, preservatives, alcohols, combinations thereof, and any other optional ingredients, may be added to the heat-transfer or antifreeze composition of the invention.

More particularly, in addition to the Bio-PDO or other biologically-derived glycol component, a typical heat transfer fluid formulation of the invention may include one or more of water from 1.0-95.0% by weight, corrosion inhibitors from 0.10% to 50.0%, foam suppressors from 0.10% to 50.0%, and/or dyes from 0.10% to 50.0%.

In a typical antifreeze fluid or coolant formulation of the invention, in addition to the Bio-PDO or other biologically-derived glycol component, such formulations may also include one or more of water from 1.0-90.0% by weight, corrosion inhibitors from 0.10% to 50.0%, foam suppressors from 0.10% to 50.0%, and dyes from 0.10% to 50.0%.
Ingredients Set forth below is a non-limiting listing of ingredients that may be used in combination with Bio-PDO in heat transfer and antifreeze formulations of the present invention. This listing is not intended to be all-inclusive, and those having skill in the art are familiar with other known ingredients that may apply to formulations of the invention.
Corrosion Inhibitors Useful corrosion inhibitors can be used in an amount sufficient to inhibit or reduce corrosion of exposed metal surfaces in contact with the engine cooling composition of the present invention, preferably in an amount of from 0.01 to 50% by weight. Preferable corrosion inhibitors include any conventionally or commercially used corrosion inhibitor, including, but not limited to, inorganic nitrates and nitrates, preferably selected from the Na, K, Mg, Ca, and Li salts; azoles selected from tolyltriazole, hydrocarbyl triazole, benzotriazole, mercaptobenzothiazole, pyrazoles, isooxazoles, isothiazoles, thiazoles, thiadiazole salts, 1,2,3-benzotriazole, 1,2,3-tolyltriazole, and Na 2-mercaptobenzothiazole; inorganic molybdates such as Na molybdate, K molybdate, Li molybdate, ammonium molybdate, ammonium dimolybdate, Mo03, heteropolymolybdates, disodium molybdate dihydrate, silicoheteropolymolybdates, and phosphoheteropolymolybdates; monocarboxylic acids, typically C3-16-carboxylic (or fatty) acids (or the corresponding alkali metal salts), esp. hexanoic, heptanoic, isoheptanoic, octanoic, 2-ethylhexanoic, nonanoic, decanoic, undecanoic, dodecanoic, and neodecanoic acids; inorganic phosphates include K2HPO4, Na2HPO4, KH2PO4, K3PO4, NaH2PO4, and Na3PO4 and mixtures thereof, for example. More preferably the corrosion inhibitor is one of the PENRAY corrosion inhibitors available from The Penray Companies, such as PENRAY 2792 (an aqueous solution of nitrites, nitrates and sodium hydroxide).

Defoamers

Defoamers are used in an amount sufficient to reduce buildup of foam or reduce foam or trapped air by causing the bubbles to burst, thus releasing the trapped air. Preferably a defoamer is used in an amount of from 0.01 to 50% by weight. One or more than one defoamer may be present. Preferable defoamers include, but are not limited to, PATCOTE 415 or 462 (an ethylene glycol n-butyl ether based defoamer made by American Ingredients Company), PLURONIC L61 (a block copolymer manufactured by BASF Corp.), DOW AF9020 (a silicone emulsion produced by Dow Chemical), ADVANTAGE 831 (a hydrocarbon oil emulsion produced by Hercules, Inc.), POLYTERGENT P32A (an EO/PO copolymer made by Olin Corp.), LANDA 5600 (oil soluble, water miscible defoamer produced by Landa Corp.) and AF-20F (a silicone oil emulsion produced by Performance Chemicals LLC), for example.

Water

The water contained in the composition can be any desired amount, preferably from 1 to 99% by weight. More preferably, the amount of water is in the range from 30 to 70% by weight, most preferably from 40 to 60% by weight. The water is preferably distilled and/or deionized. Preferably, the water is deionized before contacting with the other components of the composition.

Colorant/Dye

The present invention composition can contain a colorant/dye in order to help a user readily distinguish the composition from colorless liquids, particularly from water. Suitable colorants can be any conventional colorant, and can be any desired color, including but not limited to orange, blue, green, red and yellow, and any combination thereof. If present, the dye can be used in any amount to provide the color desired, preferably from 0.01 to 50% by weight. One or more than one dye may be present. More preferably, any light stable, transparent water soluble organic dye is suitable, including but not limited to, Acid Red dyes, methylene blue, uranine dye, wool yellow dye and rhodamine dye, with dyes such as 15189 EOSINE OJ (an Acid Red 87 based dye commercially available from Chemcentral Dyes and Pigments) being particularly preferred.

Fluorosurfactant

The composition of the present invention further comprises at least one fluorosurfactant in an amount of 0.001 to 50% by weight. The fluorosurfactant desirably causes a reduction in contact angle (e.g., droplet height) compared to an untreated water/glycol mixture, modifies the surface properties of liquids or solids, or reduces surface tension in a fluid or the interfacial tension between two immiscible fluids, for example oil and water. The measurement of contact angle and/or surface tension is known in the art. The terms, fluorosurfactant and fluorinated surfactant are used interchangeably herein. Preferably, the fluorosurfactant is soluble in water. Preferable fluorosurfactants include, but are not limited to, the ZONYL fluorosurfactants (anionic, nonionic and amphoteric fluorinated surfactants) including, but not limited to, ZONYL FSA, FSE, FSJ, FSP, TBS, FSO, FSH, FSN, FSD and FSK, more preferably the non-ionic ZONYL fluorosurfactants, most preferably ZONYL FSH, FSN or FSP (typically mixtures of a fluoroalkyl alcohol substituted polyethylene glycol with water and a glycol or glycol ether such as dipropylene glycol methyl ether) (all commercially available from DuPont). The fluorosurfactant can be used alone, or can be combined with other fluorosurfactants or non-fluorine containing surfactants as desired.

Esters

Esters can function as many of the above noted ingredients. While those in those having skill in the art can readily determine which esters are most appropriate to provide a particularly desired function, applications specifically note that esters used in this invention may include the esters produced, including all the appropriate conjugate mono and diesters, from biologically-derived 1,3 propanediol using organic carboxylic acids. Some esters in particular that are produced include propanediol distearate and monostearate, propandiol dilaurate and monolaurate, propanediol dioleate and monooleate, propanediol divalerate and monovalerate, propanediol dicaprylate and monocaprylate, propanediol dimyristate and monomyristate, propanediol dipalmitate and monopalmitate, propanediol dibehenate and monobehenate, propanediol adipate, propanediol maleate, propanediol dioxalate, propanediol dibenzoate, propanediol diacetate, and all mixtures thereof.

Additional Ingredients

The present composition may optionally include one or more other additives. These include, but are not limited to, for example, alkali metal borates as corrosion-inhibitors such as disclosed in U.S. Pat. Nos. 4,149,985, 2,566,923, 3,960,740, 2,373,570, and 2,815,328; alkali metal sebacates as corrosion inhibitors such as disclosed in U.S. Pat. No. 2,726,215, U.K. Patent 1,004,259, U.S. Pat. Nos. 4,382,008, 4,561,990, 4,587, 028, and 4,588,513; alkali metal molybdates as corrosion-inhibitors such as disclosed in U.S. Pat. Nos. 2,147,409 and 4,561,990; alkali metal mercaptobenzothiazole such as disclosed in U.S. Pat. Nos. 2,815,328, 4,455,248, 4,414,126, and 4,545,925; alkali metal nitrates as corrosion-inhibitors such as disclosed in U.S. Pat. Nos. 2,815,328, 4,508,684, 4,455, 248, and 4,587,028; tolyltriazole such as disclosed in U.S. Pat. Nos. 4,242,214, 2,587,028, 4,382,008, and U.K. Patent 1,004,259; alkali metal silicates such as disclosed in U.S. Pat. Nos. 2,815,328, 4,242,214, 4,382,008, 4,382,870, 4,455,248, and 4,149,985, the relevant portions of each of which are hereby incorporated by reference.

Natural Ingredients

The heat transfer or antifreeze compositions of the invention can contain any natural ingredients where appropriate. Natural ingredients include any natural or nature-derived ingredients similar in composition or in function to any of the ingredients listed above.

All of the compositions and methods disclosed and claimed herein can be made and executed without undue experimentation in light of the present disclosure. While the compositions and methods of the present disclosure have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents, which are chemically related, may be substituted for the agents described herein while the same or similar results would be achieved. All such similar substitutes and modifications apparent to those skilled in the art are deemed to be within the spirit, scope, and concept of the invention as defined by the appended claims.

EXAMPLES

The present invention is further defined in the following Examples. It should be understood that these Examples, while indicating preferred embodiments of the invention, are given by way of illustration only. From the above discussion and these Examples, one skilled in the art can ascertain the preferred features of this invention, and without departing from the spirit and scope thereof, can make various changes and modifications of the invention to adapt it to various uses and conditions.

Example 1

| Engine Coolant | |
|---|---|
| Ingredient | Weight Percent |
| Bio-PDO | 30-60 |
| Deionized water | 36.5-69 |
| Pyrrole compound | 0.05-0.22 |
| Polymer | 0.60-1.60 |
| Polyacrylic acid | 0.05-0.20 |
| Sodium benzoate | 0.15-0.90 |
| AEO9 purging agent | 0.05-0.10 |
| Monocarboxylic acid | 0.05-0.25 |
| Dicarboxylic salt | 0.05-0.25 |
| 4-hydroxy Bu benzoate | 0.0001-0.0002 |
| Antifoam | 0.0001-0.0002 |
| Green dye | 0.0001-0.0002 |

Example 2

| Heat transfer liquids with glass corrosion protection | |
|---|---|
| Ingredient | Weight Percent |
| Bio-PDO | 94% |
| Polyacrylic acid | <0.5% |
| KOH (50%) | <0.3% |
| Tolutriazole | <0.2% |
| Benzotriazole | <0.1% |
| Sodium molybdate dehydrate | <0.1 |
| Hydroxyalkylamine | <5% |
| Antifoam | 0.004% |
| Sodium metasilicate | 0.2% |
| Water | q.s. to 100% |

Example 3

| Antifreeze and/or coolant | |
|---|---|
| Ingredient | Wt. % |
| Bio-PDO | 0.1-99.9% |
| 3-hydroxypropionic acid salts or esters | 0.1-99.9% |

Example 4

| Anhydrous phosphate-free antifreeze | |
|---|---|
| Ingredient | Wt. % |
| Bio-PDO | 92-98% |
| Borate (as B4O7) | 0.16-0.81% |
| Molybdate (as MoO4) | 0.13-0.66% |
| Nitrate (as NO3) | 0.073-0.36% |
| Nitrite (as NO2) | 0.67-0.33% |
| Tolyltriazole | 0.15-0.50% |
| Silicate (as SiO2) | 0.014-0.07% |

Example 5

| Antifreeze composition for diesel engines | |
|---|---|
| Ingredient | Wt. % |
| Monobasic carboxylic acid | 0.1-10% |
| Nitrate salt | 0.01-10% |
| Nitrite salt | 0.001-10% |
| Azole | 0.01-5.0% |
| Molybdate | 0.001-5.0% |
| Silicone-silicate copolymer | 0.01-10% |
| Poly(vinylpyrrolidone) | 0.001-5.0% |
| Bio-PDO | q.s. to 100% |

Example 6

| Aqueous antifreeze coolant | |
|---|---|
| Ingredient | Wt. % |
| Sodium polyacrylate/polyacrylic acid | 0.001-10% |
| Nitrate salt | 0.001-10% |
| Nitrite salt | 0.001-10% |
| Azole | 0.001-10% |
| Polysilicate | 0.001-10% |
| Phosphate | 0.001-10% |
| Molybdate | 0.001-10% |
| Bio-PDO | q.s. to 100 |

Example 7

Antifreeze-type coolant

| Ingredient | Wt. % |
| --- | --- |
| Bio-PDO | 93% |
| 2-ethylhexanoic acid | 3.1% |
| Neodecanoic acid | 1.1% |
| Sodium nitrate | 0.2% |
| Sodium nitrite | 0.4% |
| Tolyltriazole | 0.09% |

Example 8

Sealing agents containing antifreeze

| Ingredient | Wt. % |
| --- | --- |
| Natural rubber latex | 55% |
| Tackifier resin emulsion | 15% |
| Bio-PDO ™ | 30% |

Example 9

Water-based coating materials applicable at freezing point

| Ingredient | Wt. % |
| --- | --- |
| Acronal YJ 2730D | 45% |
| Solvent-soluble resin | 15% |
| Bio-PDO | 2% |
| Methanol | 3% |
| Butoxyethanol | 5% |

Example 10

Antifreeze foam

| Ingredient | Wt. % |
| --- | --- |
| Bio-PDO ™ | 45% |
| Isopropanol | 40% |
| Polyethylene glycol stearyl ether | 5% |
| Dichlorodifluoromethane | 7.5% |
| Propane | 2.5% |

Example 11

Antifreeze for freezing of foods

| Ingredient | Wt. % |
| --- | --- |
| Ethanol | 49% |
| Water | 48.5% |
| Polydimethylsiloxane | 0.2% |
| Bio-PDO | 1.7% |
| Sodium malate | 0.3% |
| Glycerin monocaprylate/caproate | 0.2% |
| Glycine | 0.1% |

Example 12

Antifreeze for solid surfaces

| Ingredient | Wt. % |
| --- | --- |
| Bio-PDO | 70.0% |
| Ethanol | 5.0% |
| EO/PO copolymer | 20.0% |
| Water | 5.0% |
| Corrosion inhibitor | 0.12% |
| Nonionic surfactant | 0.5% |
| Perfume | 0.1% |

Example 13

Liquid antifreeze for agrochemicals

| Ingredient | Wt. % |
| --- | --- |
| 2,4-dichlorophenoxyacetic acid | 43% |
| Sulfonated lignin | 1.5% |
| Bio-PDO | 2% |
| Aluminum hydroxide gel (10%) | 9.0% |
| Hydroxypropyl guar | 0.2% |
| Antifoam agent | 0.1% |
| Water | 44.2% |

Example 14

Antifreeze for fuel tanks

| Ingredient | Wt. % |
| --- | --- |
| Isopropanol | 69.95% |
| Bio-PDO | 29.95% |
| Triethanolamine | 0.05% |
| Sodium nitrate | 0.03% |
| Benzotriazoleamine salt | 0.02% |

Example 15

| Heat transfer fluid for electrically heated boilers | |
| --- | --- |
| Ingredient | Wt. % |
| Bio-PDO | 30-55% |
| Sodium phosphate | 0.04-0.10% |
| Ammonium molybdate | 0.03-0.09% |
| Water | q.s. to 100% |

Example 16

| Concentrate for preparing antifreezes and heat-transfer agents | |
| --- | --- |
| Ingredient | Wt. % |
| Phosphoric acid (78%) | 2.0-20.0% |
| Triethanolamine | 10.0-60.0% |
| 2-mercaptobenzothiazole sodium salt | 0.1-1.2% |
| EDTA disodium salt dihydrate | 0.5-1.5% |
| Caprolactam | 0.1-3.0% |
| 1,4-dihydroxybenzene | 0.001-3.0% |
| Phosphite P-24 | 0.001-0.005% |
| Antifoaming agent | 0.02-0.03% |
| Dye | 0.05-0.06% |
| Butoxyethanol | 0.2-0.3% |
| Water | 10.0-35.0% |
| Bio-PDO | q.s. to 100% |

Example 17

| Heat transfer fluid for solar installations | |
| --- | --- |
| Ingredient | Wt. % |
| Triethylene glycol | 45-98% |
| Bio-PDO | 1-55% |
| Corrosion inhibitors | 1-6% |

Example 18

| Preparation of a non-foaming liquid heat transfer agent | |
| --- | --- |
| Ingredient | Wt. % |
| Bio-PDO | 96.42% |
| Sodium salt of poly(acrylic acid) | 0.02% |
| Sodium borate | 2% |
| Sodium benzoate | 1% |
| Sodium nitrite | 0.15% |
| Sodium nitrate | 0.1% |
| Benzotriazole | 0.2% |
| Poly(dimethylsiloxane) | 0.01% |
| Sodium silicate | 0.1% |

Example 19

| Heat transfer refrigeration fluid | |
| --- | --- |
| Ingredient | Wt. % |
| Bio-PDO | 45% |
| Propylene carbonate | 5% |
| H2O | 50% |

Example 20

| Antifreeze composition | |
| --- | --- |
| Ingredient | Wt. % |
| Part A | |
| Cellulose gum | 0.5% |
| Alginic acid | 0.5% |
| Gelatin | 2% |
| Water | 47% |
| Bio-PDO | 50% |
| Part B | |
| Ferric chloride | 5% |
| Water | 45% |
| Bio-PDO | 50% |

Example 21

| Engine Coolant | |
| --- | --- |
| Bio-PDO | 49.74% |
| Water | 48.76% |
| Fluoro-surfactant | 0.01% |
| Corrosion inhibitor | 1.29% |
| Defoamer | 0.08% |
| Dye | 0.12% |

Example 22

Heat Transfer Composite

The composite comprises Bio-PDO, and/or glycerin, and water as major components, and contains 0.5-5.0 wt. % of C8-12 aliphatic dibasic acids and the alkali metal salts, 0.5-5.0 wt. % of benzoic acid and the alkali metal salts, 0.05-1.0 wt. % of triazoles, and 0.01-0.5 wt. % of thiazoles.

Example 23

Reusable Thermal Pack and Flow Retardant Gel

The thermal pack for therapeutic use includes a gel pad in a 1st flexible sealed bag connected to a pressure chamber from a 2nd flexible sealed bag which can be inflated. The gel comprises clay (bentonite) and Bio-PDO, and includes a fibrous material to prevent flow and increase heat capacity.

Example 24

Non-Aqueous Heat Transfer Fluid

The invention is directed to a heat transfer system comprising a heat transfer fluid. The heat transfer fluid comprising non-buffered Bio-PDO, and at least one Bio-PDO™ soluble additive selected from the group consisting of a molybdate salt, a nitrate compound and an azole compound.

Example 25

Antifreeze Coolant Composition for High Temperature Applications

The present invention comprises an improved antifreeze coolant composition with certain additives (0.01 wt. % to 5.0 wt. %) that serve to increase the thermal stability of the Bio-PDO™ component of a Bio-PDO/water (5-95:95-5) coolant composition and to reduce the tendency of the Bio-PDO component to degrade under elevated thermal conditions. These additives comprise organic compounds with a carboxylic acid moiety and a hydroxyl moiety, and also tricarballylic acid. Another aspect of this invention concerns a method for improving the stability of the Bio-PDO component of a Bio-PDO/water coolant composition in engine cooling/heating systems by formulating a Bio-PDO/water coolant composition with the thermal stability additive to form an improved coolant composition, and contacting the engine cooling/heating system with the improved coolant composition.

Example 26

| Cryopreservation composition of Bio-PDO and a vehicle solution | |
|---|---|
| Component | Concentration |
| Bio-PDO | 0.05M to about 6.0M |
| | 0.5M to about 4.0M (more preferred) |
| | 0.5M to about 3.0M (most preferred) |
| EuroCollins solution: | |
| Sodium (Na+) | 10 mM |
| Potassium (K+) | 115 mM |
| Chloride (Cl−) | 15 mM |
| Phosphate monobasic (H2PO4−) | 15 mM |
| Phosphate dibasic (HPO42−) | 42.5 mM |
| Bicarbonate (HCO3) | 10 mM |
| Glucose | 194 mM |

What is claimed:

1. A heat transfer or antifreeze composition comprising 1,3-propanediol, an anti-corrosive in an amount of from 0.01 to 50% by weight, a defoamer in an amount of from 0.01 to 50% by weight, and a dye, wherein said 1,3-propanediol is biologically-derived, comprises peroxides wherein said peroxides concentration is less than about 10 ppm of said 1,3-propanediol, and has a bio-based carbon content of at least 1%, and wherein said composition has a lower anthropogenic $CO_2$ emission profile as compared to a composition comprising 1,3-propanediol with a bio-based carbon content of 0%.

2. The heat transfer or antifreeze composition of claim 1 further comprising water.

3. The heat transfer or antifreeze composition of claim 1 wherein the 1,3-propanediol has at least 5% biobased carbon.

4. The heat transfer or antifreeze composition of claim 1 wherein the 1,3-propanediol has at least 10% biobased carbon.

5. The heat transfer or antifreeze composition of claim 1 wherein the 1,3-propanediol has at least 25% biobased carbon.

6. The heat transfer or antifreeze composition of claim 1 wherein the 1,3-propanediol has at least 50% biobased carbon.

7. The heat transfer or antifreeze composition of claim 1 wherein the 1,3-propanediol has at least 75% biobased carbon.

8. The heat transfer or antifreeze composition of claim 1 wherein the 1,3-propanediol has at least 90% biobased carbon.

9. The heat transfer or antifreeze composition of claim 1 wherein the 1,3-propanediol has at least 99% biobased carbon.

10. The heat transfer or antifreeze composition of claim 1 wherein the 1,3-propanediol has 100% biobased carbon.

11. The heat transfer or antifreeze composition of claim 1 wherein the biologically-derived 1,3-propanediol is biologically produced through a fermentation process.

12. A heat transfer or antifreeze composition comprising 1,3-propanediol, an anti-corrosive in an amount of from 0.01 to 50% by weight, and a dye, wherein said 1,3-propanediol is biologically-derived, comprises peroxides wherein said peroxides concentration is less than about 10 ppm of said 1,3-propanediol, and has a bio-based carbon content of at least 1%, wherein said composition has a lower anthropogenic $CO_2$ emission profile as compared to a composition comprising 1,3-propanediol with a bio-based carbon content of 0%, and wherein the anti-corrosive is selected from the group consisting of inorganic nitrates and nitrates, tolyltriazole, hydrocarbyl triazole, benzotriazole, mercaptobenzothiazole, pyrazoles, isooxazoles, isothiazoles, thiazoles, thiadiazole salts, 1,2,3-benzotriazole, 1,2,3-tolyltriazole, Na 2-mercaptobenzothiazole, inorganic molybdates, monocarboxylic acids, inorganic phosphates, and aqueous solutions of nitrites, nitrates and sodium hydroxide.

13. The heat transfer or antifreeze composition of claim 12 wherein the 1,3-propanediol has at least 5% biobased carbon.

14. The heat transfer or antifreeze composition of claim 12 wherein the 1,3-propanediol has at least 10% biobased carbon.

15. The heat transfer or antifreeze composition of claim 12 wherein the 1,3-propanediol has at least 25% biobased carbon.

16. The heat transfer or antifreeze composition of claim 12 wherein the 1,3-propanediol has at least 50% biobased carbon.

17. The heat transfer or antifreeze composition of claim 12 wherein the 1,3-propanediol has at least 75% biobased carbon.

18. The heat transfer or antifreeze composition of claim 12 wherein the 1,3-propanediol has at least 90% biobased carbon.

19. The heat transfer or antifreeze composition of claim 12 wherein the 1,3-propanediol has at least 99% biobased carbon.

20. The heat transfer or antifreeze composition of claim 12 wherein the 1,3-propanediol has 100% biobased carbon.

21. The heat transfer or antifreeze composition of claim 12 wherein the biologically-derived 1,3-propanediol is biologically produced through a fermentation process.

22. The heat transfer or antifreeze composition of claim 1, wherein the defoamer is a polymer based or an oil based defoamer.

23. The heat transfer or antifreeze composition of claim 22, wherein the polymer based defoamer is selected from the group consisting of a block copolymer based defoamer, a silicone emulsion based defoamer, an EO/PO copolymer based defoamer, and a silicone oil emulsion based defoamer.

24. The heat transfer or antifreeze composition of claim 22, wherein the oil based defoamer is selected from the group consisting of an ethylene glycol n-butyl ether based defoamer, a hydrocarbon oil emulsion based defoamer, and an oil soluble, water miscible based defoamer.

25. The heat transfer or antifreeze composition of claim 1, wherein the anti-corrosive is selected from the group consisting of inorganic nitrates and nitrates, tolyltriazole, hydrocarbyl triazole, benzotriazole, mercaptobenzothiazole, pyrazoles, isooxazoles, isothiazoles, thiazoles, thiadiazole salts, 1,2,3-benzotriazole, 1,2,3-tolyltriazole, Na 2-mercaptobenzothiazole, inorganic molybdates, monocarboxylic acids, inorganic phosphates, and aqueous solutions of nitrites, nitrates and sodium hydroxide.

26. A heat transfer or antifreeze composition comprising 1,3-propanediol, an anti-corrosive in an amount of from 0.01 to 50% by weight, and a defoamer in an amount of from 0.01 to 50% by weight, wherein said 1,3-propanediol is biologically-derived, comprises peroxides wherein said peroxides concentration is less than about 10 ppm of said 1,3-propanediol, and has a bio-based carbon content of at least 1%, wherein said composition has a lower anthropogenic $CO_2$ emission profile as compared to a composition comprising 1,3-propanediol with a bio-based carbon content of 0%, and wherein the defoamer is a polymer based or an oil based defoamer.

27. The heat transfer or antifreeze composition of claim 26, wherein the polymer based defoamer is selected from the group consisting of a block copolymer based defoamer, a silicone emulsion based defoamer, an EO/PO copolymer based defoamer, and a silicone oil emulsion based defoamer.

28. The heat transfer or antifreeze composition of claim 26, wherein the oil based defoamer is selected from the group consisting of an ethylene glycol n-butyl ether based defoamer, a hydrocarbon oil emulsion based defoamer, and an oil soluble, water miscible based defoamer.

* * * * *